US009358255B2

(12) United States Patent
Dunworth et al.

(10) Patent No.: US 9,358,255 B2
(45) Date of Patent: Jun. 7, 2016

(54) METHODS AND DEVICES FOR OBTAINING AND PROVIDING COMBINATION CELL THERAPY

(71) Applicant: SpineSmith Partners, L.P., Austin, TX (US)

(72) Inventors: Kevin Dunworth, Austin, TX (US); Richard J. Kana, Lexington, TX (US); Theodore Sand, Austin, TX (US); Matthew Murphy, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 40 days.

(21) Appl. No.: 14/049,026

(22) Filed: Oct. 8, 2013

(65) Prior Publication Data

US 2014/0099288 A1    Apr. 10, 2014

Related U.S. Application Data

(60) Provisional application No. 61/710,812, filed on Oct. 8, 2012, provisional application No. 61/713,739, filed on Oct. 15, 2012.

(51) Int. Cl.
*A61K 35/12* (2015.01)
*A61K 35/35* (2015.01)
*A61K 35/14* (2015.01)
*A61K 35/28* (2015.01)
*C12N 5/0775* (2010.01)

(52) U.S. Cl.
CPC ................. *A61K 35/35* (2013.01); *A61K 35/14* (2013.01); *A61K 35/28* (2013.01); *C12N 5/0663* (2013.01); *C12N 5/0667* (2013.01); *C12N 2502/1358* (2013.01); *C12N 2502/1382* (2013.01)

(58) Field of Classification Search
None
See application file for complete search history.

(56) References Cited

U.S. PATENT DOCUMENTS

2005/0025755 A1* 2/2005 Hedrick et al. ............ 424/93.21
2008/0193424 A1* 8/2008 McKale et al. ............. 424/93.7
2009/0036841 A1* 2/2009 McKale et al. ............. 604/266

* cited by examiner

*Primary Examiner* — Ralph Gitomer
*Assistant Examiner* — Trent Clarke
(74) *Attorney, Agent, or Firm* — Winstead PC

(57) ABSTRACT

The invention is directed to a method for isolating stromal cells to form a therapeutic composition; and administering said therapeutic composition to the subject. A further embodiment of the invention is directed to therapeutic compositions comprising isolated stromal cells.

11 Claims, 7 Drawing Sheets

METHODS AND DEVICES FOR OBTAINING AND PROVIDING COMBINATION CELL THERAPY

CROSS-REFERENCES TO RELATED APPLICATIONS

This application claims the benefit under 35 U.S.C. §119 (e) of U.S. Provisional Patent Application No. 61/710,812 filed Oct. 8, 2012, and U.S. Provisional Patent Application No. 61/713,739 filed Oct. 15, 2012, each of which are incorporated herein by reference in its entirety as if fully set forth herein.

BACKGROUND OF THE INVENTION

Cell therapy has been practiced for more than 60 years, starting with the transplantation of "tissue-matched" bone marrow units obtained from bone marrow donors. Additional cell-based therapy options include the collection and transplantation of cord blood units obtained from newborns. Both of these types of cell therapy require the matching of donor cell material with a potential recipient. This is a laborious process and can result in mismatched transplants, endangering the life of the recipient. Other approaches for cell therapy involve collecting cellular material from donors and culturing a single type of cell isolated from those donor materials to produce enough cells that they can be placed in a "bottle" and stored under specialized conditions for use in unrelated recipients. The advantage of the use of allogeneic cells is that they can be stored and are, in theory, available whenever a patient requires a treatment. There are numerous issues with "cells in a bottle", including the lack of clear cut therapeutic efficacy in humans, the early stage of clinical evaluation of allogeneic products so efficacy has yet to be established, the risks of placing "foreign" DNA in a patient and the possibility of disease transmission. In contrast to all of the foregoing limitations and liabilities, it is possible to obtain a patient's own therapeutic cells (i.e., autologous) while the treatment procedure is on-going and return a concentrated form of the autologous cells to the patient to promote a therapeutic benefit. The invention disclosed herein sets out the approach for providing a combination of autologous cells obtained from two sources of tissue for use at point-of-care (POC), which will have an improved therapeutic outcome compared to the use of cells from a single source of tissue.

The collection of cell populations from multiple tissue depots in the body can be performed in treatment rooms or surgical operating rooms. For example, collecting cells from the bone marrow involves, at least, conscious sedation and localized topical anesthetic at the site of the bone marrow collection. The BMC that is generated in this process contains a variety of types of cells, including hematopoietic stem cells (HSC), mesenchymal stem cells (MSC), endothelial progenitor cells (EPC), stromal cells, and adult cells (including "white" blood cells, megakarocytes, adult platelets, and red blood cells, among others). Collecting cells from a subcutaneous layer (i.e., adipose layer) provides another source of cells, similar in most respects to the preparations obtained from bone marrow, except that there are very few HSCs present, but there is a higher level of MSCs in cell preparations obtained from adipose tissue. Mechanically-released cells found in fluid collected during a traditional liposuction procedure mirror the types of cells obtained when adipose tissue itself is digested with enzymes to release cells. There are many commercial systems and approaches in use for collecting adipose tissue from subcutaneous layers in the human. Manual methods include the syringes and cannulae sold by Tulip Medical Company (CA). A power-assisted liposuction (PAL) system is commercially offered by MicroAire Corp. The PAL system operates by medium frequency oscillations of the suction cannula, which is claimed to provide more uniform fat removal. Another commercial system is available from BodyJet (USA), which involves the use of a jet of water that is capable of "liquefying" the fat tissue prior to removal. All such systems operate with the use of significant levels of vacuum, approximately −21 in Hg. A common feature of all of these approaches is that they result in the collection of both fat tissue and fluid introduced during the procedure.

The claimed invention involves the combination of these two cell types obtained from the same patient during a "single surgical procedure", thereby providing an advantage to the patient of therapeutic cell preparations from two tissue sources. The combination of cell types affords the patient the best chance of achieving a therapeutic benefit compared to using one or the other cell preparations singly.

In addition to there being some differences in the types of cells present in each of the cell preparations (HSCs in bone marrow, higher frequencies of MSCs in adipose), emerging evidence suggests that potentially the cell preparations are able to function in vivo in unique ways. It has been shown that cultured cell preparations of MSCs from adipose tissue compared to MSCs from bone marrow were better able to recapitulate the bone marrow of radio-ablated recipient mice when the two types of cells were implanted singly into long bone cavities. The data suggests that adipose tissue-derived cells can communicate with HSCs in order to potentiate a therapeutic benefit: faster and more prolific re-capitulation of bone marrow. Consequently, the combination of cells from the bone marrow along with cells from the subcutaneous tissue should provide for an enhanced opportunity for the patient to derive a therapeutic benefit.

SUMMARY OF THE INVENTION

An embodiment of the invention is directed to a method for treating a human subject, the method comprising: isolating stromal cells compatible with the subject; combining said stromal cells to form a therapeutic composition; and administering said therapeutic composition to the subject.

A further embodiment of the invention is directed to therapeutic compositions comprising isolated stromal cells. Another embodiment of the invention includes washing the stromal cells at least once with a fluid selected from the group consisting of platelet-rich plasma, platelet-poor plasma, concentrated platelet-poor plasma, whole blood, and combinations thereof. In another embodiment, the isolated stromal cells are able to differentiate into cells selected from the group consisting of chondrocytes, endothelial cells, osteoblasts, myocytes, neural cells, glial cells, adipocytes, pericytes, cardiomyocytes, epithelial cells, fibroblasts, and combinations thereof. In yet another embodiment, the method includes administering to the subject an additive selected from the group consisting of a cytokine, bioactive material, scaffold, buffer, or combinations thereof.

DETAILED DESCRIPTION OF EXEMPLARY EMBODIMENTS OF THE INVENTION

An embodiment of the invention is directed to a method for treating a human subject, the method comprising: obtaining blood compatible with the subject; fractionating said blood to produce a blood component, said blood component selected from the group consisting of platelet-poor plasma, concentrated platelet-poor plasma, platelet-rich plasma, and combinations thereof; obtaining stromal cells compatible with the subject; combining said stromal cells and said blood component to form a therapeutic composition; and administering said therapeutic composition to the subject.

Other embodiments of the invention are directed to a therapeutic composition comprising: isolated stromal cells; and a blood component, wherein said blood component is selected from the group consisting of platelet-poor plasma, concentrated platelet-poor plasma, platelet-rich plasma, whole blood, and combinations thereof.

Figure 1:
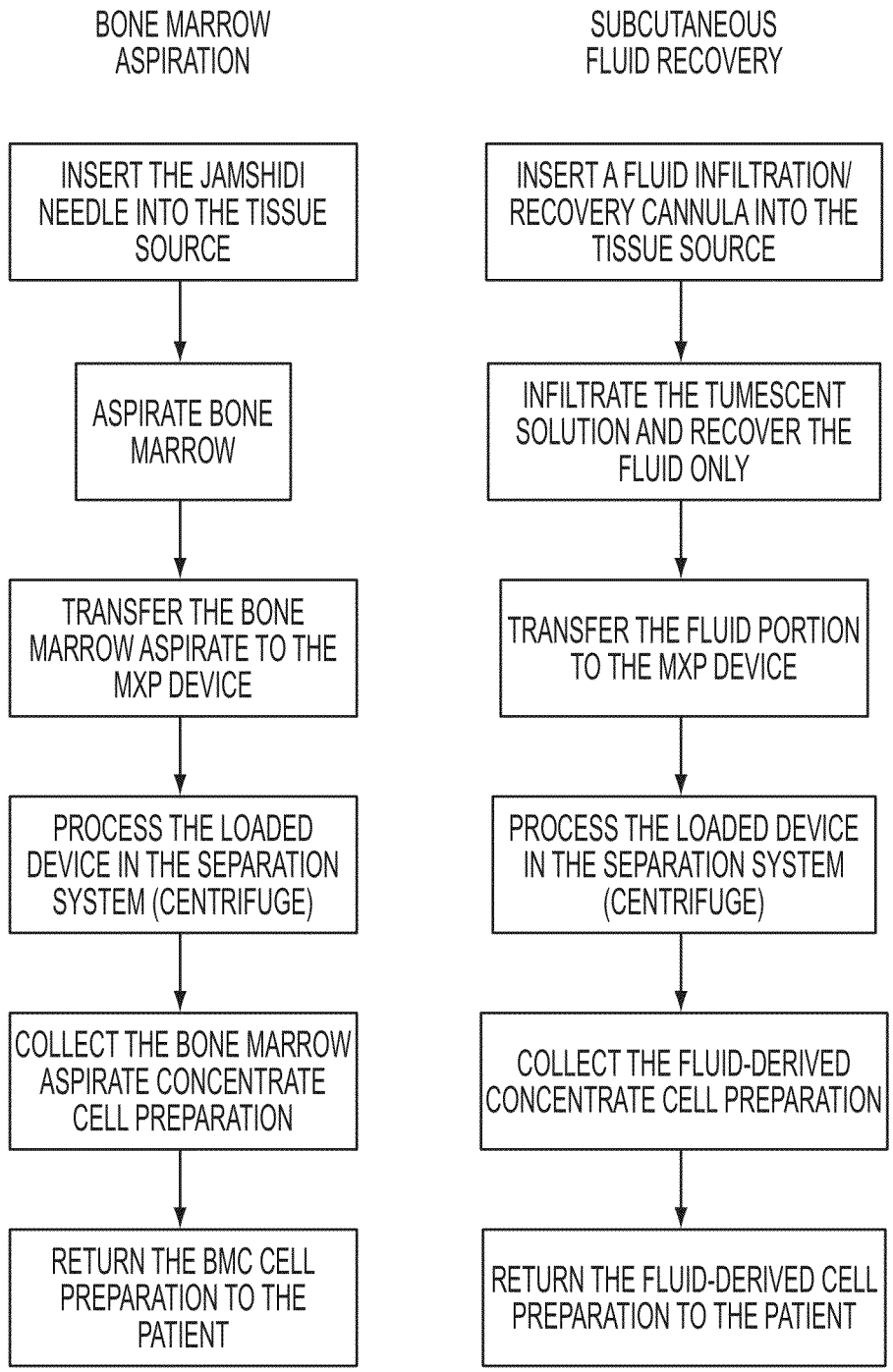
FIG. 1 depicts a schematic flow diagram of the steps involved in the collection and generation of bone marrow concentrate (BMC) and stromal vascular fraction (SVF), in accordance with an embodiment of the invention.

The steps associated with the collection and processing of bone marrow and mechanically-released cells from subcutaneous tissue layers is set forth in FIG. 1. In certain embodiments of the invention, both procedures are performed simultaneously on a patient during a single surgical procedure.

Bone Marrow Collection and Processing

Bone marrow aspirate is the cell-containing "fluid" obtained when a bone marrow compartment (i.e., the iliac crest) is punctured with a large bore needle and a vacuum is applied.

The resulting cell suspension obtained after a volume of bone marrow aspirate is processed in a centrifugation-type processing system from which the "buffy coat" (regenerative cells and platelets) is collected, is the bone marrow concentrate.

Methodology:

The contents of a Bone Marrow Aspirate Pack and the appropriate number of ART21 devices are passed to the sterile field. Each processing device is intended to be used with 60 cc of collected bone marrow aspirate. 30 cc syringes and "butterflies" are transferred in order to perform the bone aspiration as described below. Two sterile cups are marked with "Heparin" or "ACD-A". The volume of the sterile syringes present on the sterile field for collecting aspirate is maintained at 1.5 times the target aspiration volume. For example, if 60 cc of bone marrow is to be collected in 30 cc syringes, there should be at least 3 30 cc syringes available.

On the sterile field, a sufficient volume of Heparin Solution (1000 U/mL) is made to allow for rinsing of the syringes and needle(s) to be used during the bone marrow aspiration. For example, if 30 cc syringes are to be used, make at least 20 cc of Heparin Solution. Place the contents of the ACD-A vial into the cup marked "ACD-A" and fill a 20 cc syringe marked "ACD-A". A "butterfly" is attached to the ACD-A syringe. Just prior to aspiration, the first aspiration syringe is rinsed with the Heparin Solution by aspirating Heparin Solution equivalent to at least half of the syringe's volume, pulling the plunger all of the way out, and rotating and rocking the syringe to ensure contact between the Heparin Solution and the inner surface of the syringe. The stylet is removed from a Jamshidi needle and attached to the first aspiration syringe. The Heparin Solution is expelled from the aspiration syringe and Jamshidi needle back into the Heparin Solution cup.

Approximately 15 cc of the Heparin Solution is loaded into the second aspiration syringe and a "butterfly" is attached. The syringe is coated as described above. The first aspiration syringe is connected to the butterfly on the 20 cc ACD-A syringe and 2 cc of the ACD-A is transferred into the first 30 cc syringe. The Jamshidi needle is inserted into the iliac crest of the patient to a depth of 6 cm, while remaining within the tables of the crest. The stylet of the Jamshidi needle is removed after it has been inserted into the iliac crest.

The first aspiration syringe is attached to the Jamshidi needle. The plunger is pulled back rapidly to the "15 cc" level to initiate bone marrow aspiration. 4-10 cc of bone marrow is collected. The needle position is rotated ninety degrees (90°) and the plunger is rapidly pulled back to the "30 cc" level to continue to aspirate bone marrow. While bone marrow is being aspirated with the first aspiration syringe, the second aspiration syringe is prepared by transferring the Heparin Solution into the third syringe via the butterfly. The second aspiration syringe is removed from the Heparin Solution butterfly and connected to the butterfly of the 20 cc ACD-A syringe. 2 cc of ACD-A is transferred into the second aspiration syringe. Once the syringe is approximately half full (15-20 cc), it is replaced with the second aspiration syringe.

As soon as a syringe is returned to the scrub tech, the contents of the syringe are transferred to a processing device present on the sterile field.

The second 30 cc syringe is attached, the needle position (90°) is rotated, and the aspiration sequence is repeated by pulling the plunger back to the "15 cc" level. 4-10 cc of bone marrow is collected. The needle position (90°) is rotated and the plunger rapidly pulled back to the "30 cc" level to continue to aspirate bone marrow. While bone marrow is being aspirated with the second aspiration syringe, the third aspiration syringe is prepared by rocking and rotating the third aspiration syringe with the Heparin Solution followed by the transfer of the Heparin Solution into a fourth 30 cc syringe via the butterfly or back into the Heparin Solution cup. The third aspiration syringe is attached to the 20 cc ACD-A syringe via the butterfly. 2 cc of ACD-A is transferred into the third syringe.

Once the second syringe is approximately half full (15-20 cc), it is replaced with the third 30 cc syringe. The Jamshidi needle is pulled back approximately 2 cm and the aspiration sequence is repeated at the new level with the third 30 cc syringe. The sequence of aspiration of two quick pulls of the plunger with a 90° rotation between pulls for each 30 cc syringe is repeated. Depending on the volume of aspirated bone marrow per draw, it is possible to collect the target volume from three levels in the first channel. If a sufficient volume has not been aspirated from the first channel, then the Jamshidi needle should be repositioned approximately 2 cm laterally from the first channel. Parallel tracts are maintained when performing multiple channel aspirations. After the last 30 cc syringe contents have been transferred to the processing device present on the sterile field, the bone marrow aspirate-loaded device should be passed off the sterile field to be processed in the centrifugation system. Exemplary centrifugation systems for processing BMA to yield bone marrow concentrate are the ART21 and MXP Systems (Celling Biosciences, Austin, Tex.).

Collection of the BMC is accomplished by attaching a receiving syringe to the processed device at a port through which the BMC is removed, and then pulling back on the plunger of the receiving syringe to recover the BMC. The volume of the BMC could vary depending on the treatment application.

Subcutaneous Tissue Layer Fluid Collection and Processing Process Using Suction Device In one preferred embodiment, the collection of cells from a patient's subcutaneous tissue layer (aka adipose tissue) comprises the use of a "suction device" that tents the layer to be probed, an infiltration cannula and a fluid recovery cannula. In another embodiment, the infiltration and recovery functions can be performed by the use of a single cannula. In another embodiment, a suction device is not employed, during the infiltration and recovery of fluid from a patient's subcutaneous layer.

Figure 2:
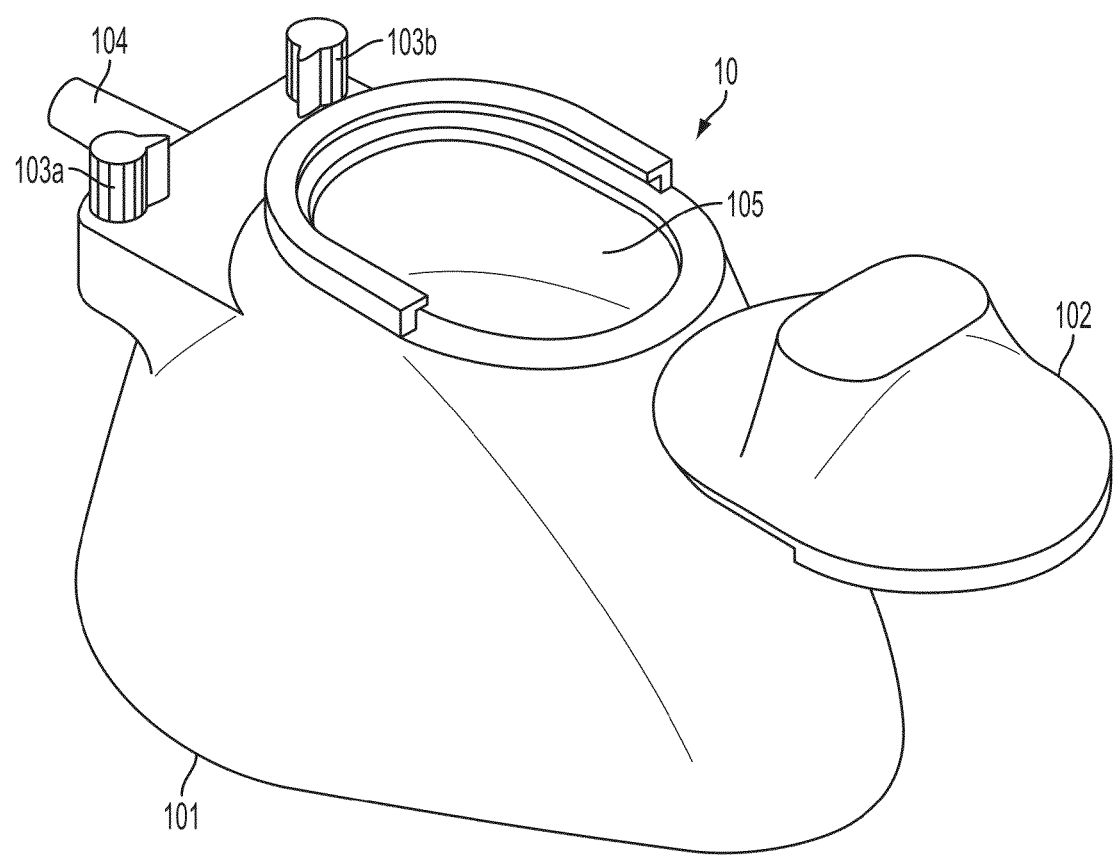
FIG. 2 depicts a suction device in accordance with an embodiment of the invention.

An embodiment of the Suction Device 10 is shown in FIG. 2. It consists of a generally trapezoidally shaped chamber 101 that has two separately controllable vacuum zones or chambers, a removable cap 102 and a single vacuum line hose 104 coupling port in a vacuum manifold with two valves. One valve in the vacuum manifold controls vacuum to the inner space of the chamber 103b, while the other valve 103a controls vacuum to a vacuum outlet that is embedded in the peripheral rim of the device that aids in sealing the device to the surface of the skin. The peripherally-located suction outlet follows the contour of the device itself. In one embodiment, the skin-contacting rim of the suction device is "flat", meaning that it does not have contours. In another embodiment, the skin-contacting edge will have a contour, which might better fit certain body shapes. As shown in FIG. 2, the hose barb location is in-line with the long axis of the device, but other orientations of the hose barb are contemplated, including a location that is perpendicular to the long axis of the device. In certain embodiments, an accessible port 105 is placed on the top surface of the suction device, which port can be opened.

Providing access through the top-mounted port enables for the facile manipulation of the tissue contained within the boundary of the suction device. Additional features that relate to the suction device in certain embodiments include the presence of an O-ring placed in a track adjacent to the peripheral suction chamber. The O-ring provides an additional element of sealing against the patient's skin, thereby making and maintaining contact between the lower edge of the suction device and the patient's skin easier to accomplish. The O-ring physically can be located on either side of the peripheral chamber. In a preferred embodiment the O-ring is located on the outer edge of the peripheral chamber.

There are a variety of cannulae in commercial use for performing liposuction. One approach is to use a cannula designed solely for infiltrating the liposuction fluid in order to perform a procedure called "tumescent liposuction". The liposuction fluid is infiltrated into the subcutaneous tissue and allowed to remain in place with no further manipulation for a period sufficient to allow the epinephrine to diffuse into the surrounding tissue to reduce bleeding. Infiltrating cannulae typically have multiple fenestrations through which the fluid flows, either through the application of manual pressure (via use of a syringe) or a mechanical means, like a pump. Fluid will be distributed in multiple locations within the subcutaneous tissue layer adjacent to the fenestrated cannula. One particular embodiment of an infiltrating cannula is a cannula in which the distal tip is blunt and closed, with fenestrations arrayed in a spiral along the distal approximately 5 cm of the cannula. Typical fenestration number is 6, but can be fewer or greater than 6.

A particular embodiment of an infiltration cannula is one designed with a tip that is splayed at the distal opening that can be positioned upward facing or downward facing if the cannula has a straight barrel or upward facing if the cannula barrel is curved. The degree of splay is limited to the diameter of the cannula barrel, which usually will be on the order of an 18 g needle, but can be as wide as 3 mm. The splayed area will not exceed the diameter of the cannula barrel, so as to present a "smooth" surface profile that will not tear fat tissue as it is inserted. The exact design of the splayed tip involves the creation of an opening that results in the delivery of a "sheet" shaped dispensed fluid profile. This is achieved by creating an angled opening of the fluid dispensing cannula barrel which is associated with a narrow opening through which the fluid must pass in order to exit the cannula barrel. In a preferred embodiment, there will be one splayed, narrow opening at the very tip of the cannula, while still maintaining a "blunt" end shape to smooth the progress of the infiltration cannula through the subcutaneous tissue layer.

The recovery cannula may be the same device as the infiltrator cannula. In a preferred embodiment, the fenestrations of the splayed, sheet-shaped dispensed fluid cannula that are arrayed along the barrel of the cannula are effectively sealed during the fluid infiltration process by a mechanical means. Once the infiltration of the target tissue zone has been achieved, the fenestrations are exposed by appropriate means and suction is applied to initiate recovery of the infiltrated fluid. In another embodiment, a separate cannula is used to perform the recovery of the infiltrated fluid. In this case, the recovery cannula will have an array of fenestrations that are laterally arranged along the barrel. In another embodiment, the fenestrations are arranged in a spiral along a length of the recovery cannula. In another embodiment, the fenestrations are tightly grouped at the distal end of the cannula, or they are spread along an 8 cm section of the recovery cannula. In all instances when a separate recovery cannula is used, the cannulae will have a closed and blunt tip. The fenestrations will not have sharp edges and the openings will be substantially circular with each fenestration presenting a small surface area in order to minimize the chance of fat tissue being collected.

The process for using the suction device, the combined infiltration/recovery cannula, or discrete infiltration and recovery cannulae is initiated by marking the skin of the patient with a surgical marking pen where the infiltration fluid will be placed. The suction device can be used to outline the target collection zone. Once the skin has been prepared, the suction device can be placed over the target zone and the vacuum initiated. Once the skin and tissue has bulged upward the vacuum can be regulated to control the degree of lift. The infiltration cannula is attached to a source of infiltration fluid and the means to pulse the fluid. This pulsing action can be achieved by a number of mechanical means known in the art, but a closed system in which the fluid is contained within a sterile environment is required. "Contact-less" pumps based on peristaltic pumping or piston-type displacement pumping can be used. The fluid to be pulsed needs to be USP grade, sterile and suitable for injection into humans. Exemplary fluids include sterile phosphate buffered saline, Lactated Ringer's (or modified Lactated Ringer's), or saline, among others.

Once the skin/tissue has been lifted, a small incision is made just outside the edge of the suction device to facilitate insertion of the infiltration cannula. If the combined infiltration/recovery cannula is used, it is inserted into the subcutaneous tissue layer with sealed fenestrations. The infiltration cannula is inserted into the patient's subcutaneous tissue layer that lies between the muscle facia below and the epidermis above. Once positioned in the subcutaneous tissue layer, the infiltration cannula is pushed into the tissue layer to one side of the tented tissue close to the edge of the suction device. Fluid is dispensed by activating a pulsing switch on the cannula wand that dispenses from 0.3 to 1.0 mL in a short period of timing, ranging from 1 second to 10 seconds. The cannula can be left in one site while the pulse of fluid is dispensed or the cannula can be pulled back slightly during the pulse period. Once a pulse of fluid has been delivered, the cannula is re-positioned within the same channel by 1-2 cm and another pulse of fluid is generated. The length of insertion of the infiltration cannula will be determined in part by the overall dimensions of the suction device, so the number of pulses per channel will depend on the length of the suction device. Once the first channel has been pulsed, the cannula is pulled back, but not out of the subcutaneous tissue layer, and re-inserted approximately 1-2 cm to the right of the first channel and the pulsing process is repeated. Proceeding in a "fan-shape" manner, the entire surface area of subcutaneous tissue is infiltrated with fluid, pivoting from the surgical incision each time in order to create another channel.

Once the process of fluid infiltration is completed, it is possible to provide mechanical stimulation of the infiltrated subcutaneous tissue by a variety of means. Pressure in the main chamber can be release and applied in a cyclic manner in order to provide some measure of mechanical tensioning and relaxation of the tented, infiltrated tissue. Pressure in the peripherally placed chamber would be maintained while the tissue is undergoing mechanical stimulation. The accessible port on the top of the suction device is opened in order to provide access to the tented, infiltrated tissue contained within the chamber of the suction device. Once opened, the tented tissue can be mechanically stimulated by a variety of devices and methods. In a preferred embodiment, a hand-held roller-type device can be placed in contact with the tissue and moved back and forth over the tissue while applying gentle pressure. Gentle pressure also can be applied by the operator's fingers. In a preferred embodiment, an ultrasonic "head" can be placed in approximation to the tented tissue and activated. The ultrasonic waves will penetrate the tented tissue creating mechanical stimulation. Other physical shapes and forms of devices which are rigid to bending forces can be used.

It also is contemplated to apply mechanical stimulation by a variety of means, as indicated in the foregoing, to the targeted site prior to the initiation of fluid infiltration.

After performing the mechanical stimulation process, if appropriate, the top access port is closed, the vacuum re-established in the chamber and the recovery cannula is inserted into the subcutaneous tissue. A low vacuum is applied once the recovery cannula is in place and fluid is collected from the infiltrated tissue. Recovered fluid is collected in a suitable sterile collection container as commonly practiced in the liposuction art. The recovery cannula is moved throughout the infiltrated tissue. During recovery of the infiltrated fluid it is possible that the access port can be opened and gentle pressure can be applied to the infiltrated tissue to promote recovery of the infiltrated fluid. The conditions of suction force created by the vacuum will be such that no tissue is collected during the fluid recovery process.

If a combined infiltration/recovery cannula is used, it may be removed to a position just inside the incision site while mechanical stimulation is performed, if appropriate. In order to initiate the recovery of infiltrated fluid with a combined infiltration/recovery cannula, the fenestrations arrayed along the barrel of the cannula will be unsealed and the splayed opening used for creating the sheet-pattern of dispensed fluid will be blocked.

In another embodiment, recovery of the infiltrated fluid is accomplished by placing the cannula (with fenestrations clustered at the distal end of the barrel) into the tented, infiltrated tissue through the top-mounted access port of the suction device.

Depending on the volume of fluid to be collected, it is possible to repeat the procedure of infiltration and recovery at additional sites on the patient's abdomen or moving to other subcutaneous tissue layers such as the flanks or lower back (also known as the "waist").

Figure 3A:
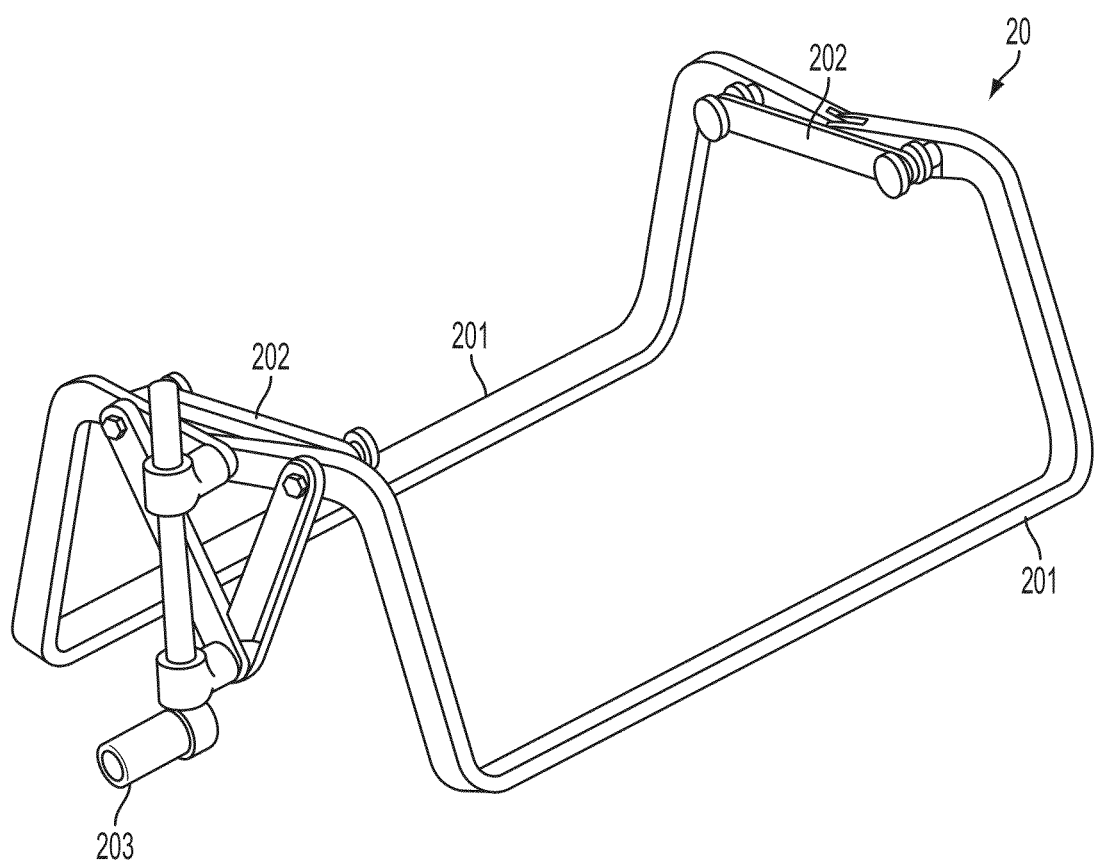
FIGS. 3A and 3B depict operational views of a clamping device in accordance with an embodiment of the invention.
Figure 3B:
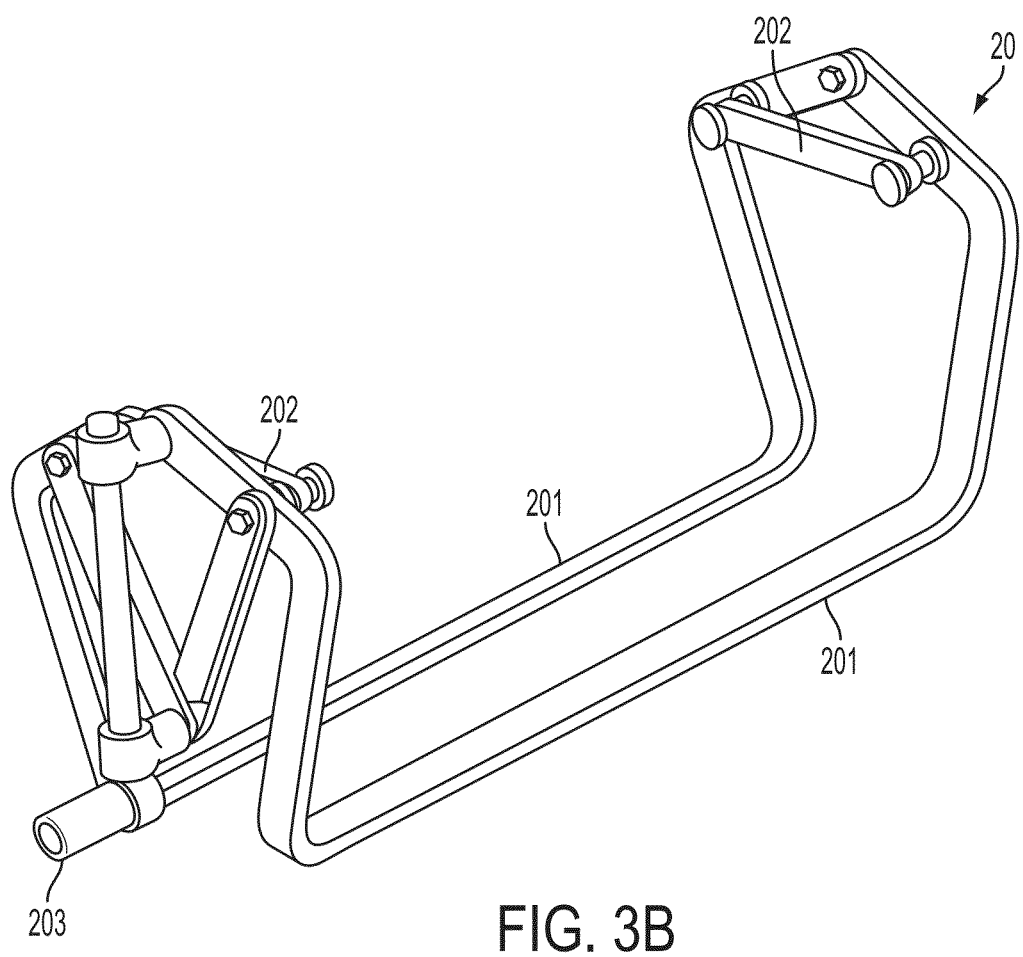

In certain embodiments of the invention, a clamping device is used in conjunction with the suction device. An embodiment of the clamping device 20 is shown in FIGS. 3A and 3B.

Figure 4A:
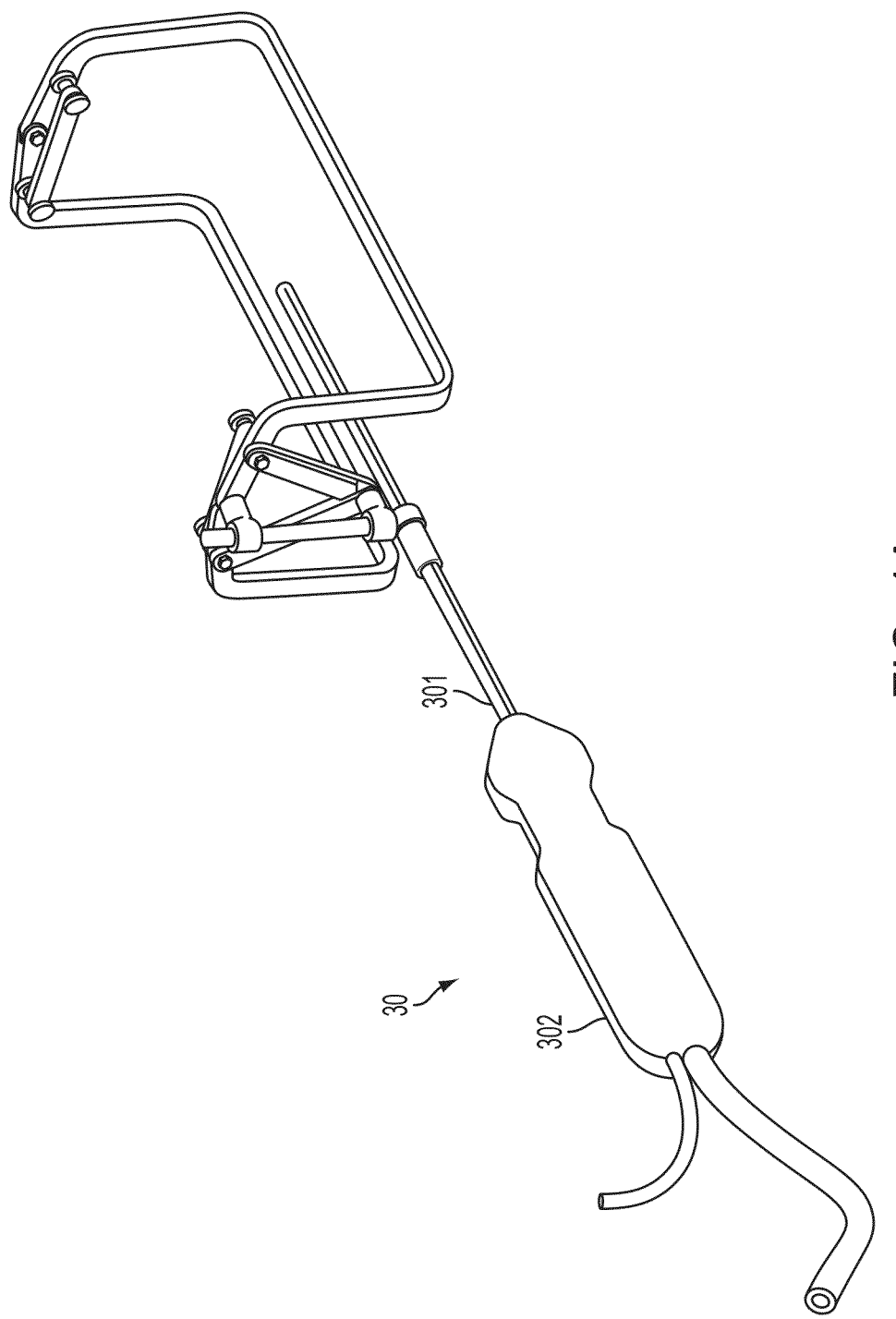
FIGS. 4A and 4B depict the operation of a cannula in a clamping device in accordance with an embodiment of the invention.
Figure 4B:
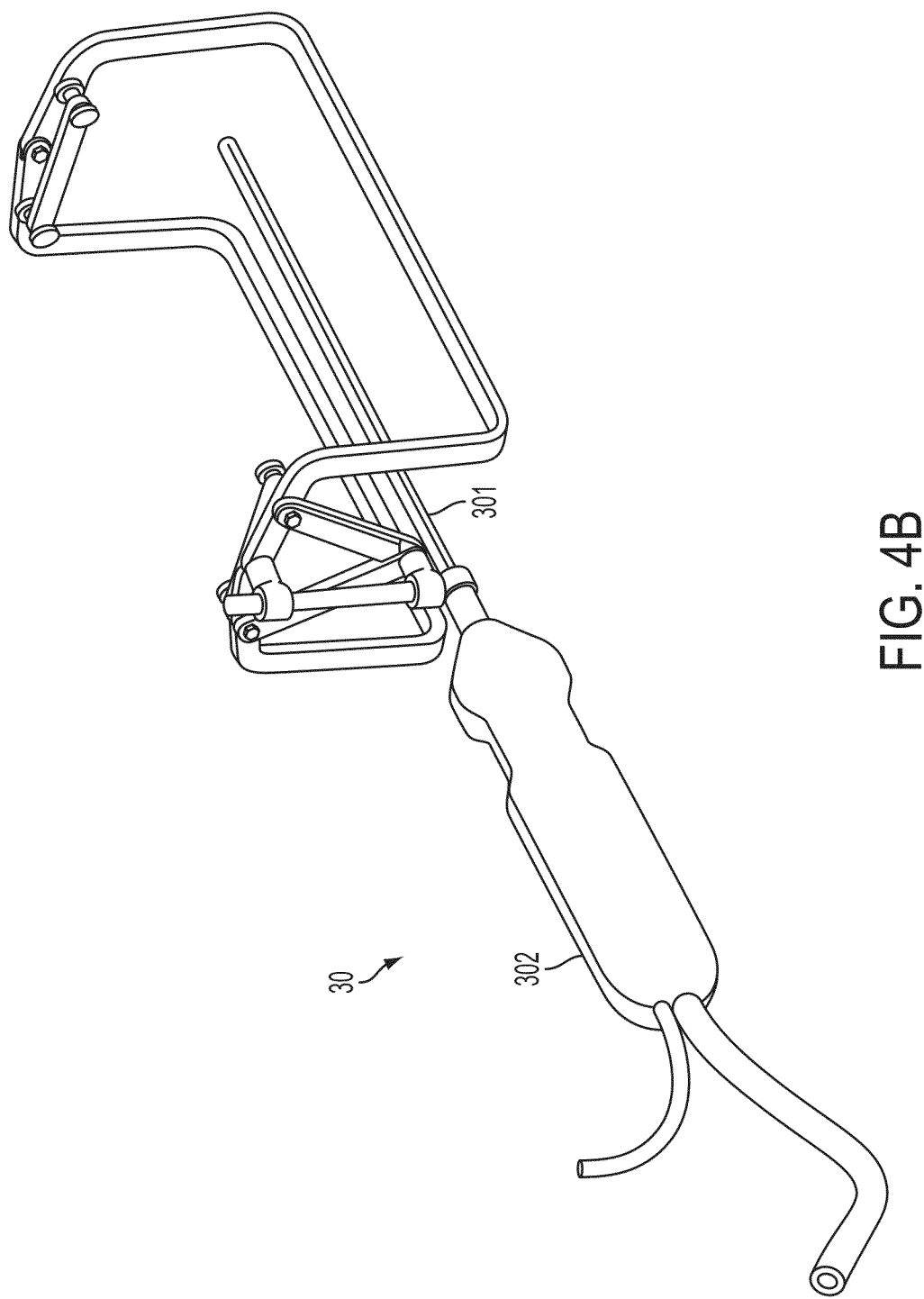

The clamping device 20 comprises two adjustable arms 201 that are used to grasp a patient's subcutaneous tissue layer in preparation for the insertion of a cannula. The arms 201 are adjusted used a spring-laden mechanism 202. The device comprises an inlet/guide 203 for the insertion of a cannula. FIG. 3A shows the clamping device 20 in an open position. FIG. 3B shows the clamping device 20 when used on a patient having low body mass index (BMI). FIG. 4A depicts the insertion of a cannula device 30 into the inlet 203 of clamping device 20. As shown in FIG. 4A, cannula device 30 comprises a cannula 301 and a guiding handle 302. With the use of the guiding handle 302, the cannula 301 is inserted into the inlet 203 of the clamping device 20. In operation, the cannula 301 is inserted first into the inlet 203 prior to entering a patient's subcutaneous tissue.

Depending upon the thickness of the subcutaneous layer that is grasped by the arms 201 of the clamping device 20, the inlet/guide 203 moves up and down in a vertical plane in order to facilitate the optimal positioning of the inlet 203 and cannula relative to the subcutaneous layer. An advantage of the clamping device 20 includes the ability to sequester a specific region of a patient's subcutaneous layer safely and in a manner that ensures repeated isolation of cells.

In one preferred embodiment, the collection of cells from a patient's subcutaneous tissue layer (aka adipose tissue) consists of the use of an infiltration cannula and a fluid recovery cannula in one embodiment, or the infiltration and recovery functions can be performed by the use of a single cannula.

Process without Suction Device

The process for performing the collection of cells from a patient's subcutaneous tissue layer in the absence of the use of a Suction Device has a number of parallel elements, but differs in specific steps in the process. The descriptions of cannulae provided previously apply in all aspects of the embodiment for processing without the Suction Device. Patient preparation differs only in the initial step of using a surgical pen to define the target zone of infiltration and collection by outlining the zone on the patient's skin. Steps involving the use of the Suction Device, including placement, manipulation of the tissue and details of the vacuum applied are not applicable. Fluid collection is initiated in the absence of the use of the Suction Device by making a small incision just outside the marked outline to facilitate insertion of the infiltration cannula. If the combined infiltration/recovery cannula is used, it should be inserted into the subcutaneous tissue layer with sealed fenestrations. The infiltration cannula is inserted into the patient's subcutaneous tissue layer that lies between the muscle facia below and the epidermis above. Once positioned in the subcutaneous tissue layer, the infiltration cannula is pushed into the tissue layer to one side of the marked zone. Fluid is dispensed by activating a pulsing switch on the cannula wand that dispenses from, for example, 0.3 to 1.0 mL in a short period of timing, ranging from 1 second to 10 seconds. The cannula can be left in one site while the pulse of fluid is dispensed or the cannula can be pulled back slightly during the pulse period. Once a pulse of fluid has been delivered, the cannula is re-positioned within the same channel by 1-2 cm and another pulse of fluid is generated. The length of insertion of the infiltration cannula will be determined in part by the overall dimensions of the outlined zone, so the number of pulses per channel will depend on the length of the outlined zone. Once the first channel has been pulsed, the cannula is pulled back, but not out of the subcutaneous tissue layer, and re-inserted approximately 0.5-1 cm to the laterally from the first channel and the pulsing process is repeated. Proceeding in a "fan-shape" manner, the entire surface area of subcutaneous tissue is infiltrated with fluid, pivoting from the surgical incision each time in order to create another channel.

Once the process of fluid infiltration is completed, it is possible to provide mechanical stimulation of the infiltrated subcutaneous tissue by a variety of means. For example, it is possible to physically massage the area manually. Alternatively, a device like the LPG can be used, which incorporates a suction/roller head that enables for deep tissue manipulation. In a preferred embodiment, a hand-held roller-type device can be placed in contact with the tissue and moved back and forth over the tissue while applying gentle pressure. In a preferred embodiment, an ultrasonic "head" can be placed in approximation to the infiltrated tissue and activated. The ultrasonic waves will penetrate the underlying tissue creating mechanical stimulation. Other physical shapes and forms of devices which are rigid to bending forces can be used to apply mechanical stimulation to the infiltrated tissue.

It also is contemplated to apply mechanical stimulation by a variety of means, as indicated in the foregoing, to the targeted site prior to the initiation of fluid infiltration.

After performing the mechanical stimulation process, the recovery cannula is inserted into the subcutaneous tissue. A low vacuum is applied once the recovery cannula is in place and fluid is collected from the infiltrated tissue. Recovered fluid is collected in a suitable sterile collection container as commonly practiced in the liposuction art. The recovery cannula is moved throughout the infiltrated tissue. During recovery of the infiltrated fluid it is possible to directly apply gentle pressure to the infiltrated tissue to promote recovery of the infiltrated fluid.

If a combined infiltration/recovery cannula is used, it may be removed to a position just inside the incision site while mechanical stimulation is performed, if appropriate. In order to initiate the recovery of infiltrated fluid with a combined infiltration/recovery cannula, the fenestrations arrayed along the barrel of the cannula will be unsealed and the splayed opening used for creating the sheet-pattern of dispensed fluid will be blocked.

Depending on the volume of fluid to be collected, it is possible to repeat the procedure of infiltration and recovery at additional sites on the patient's abdomen or moving to other subcutaneous tissue layers such as the flanks or lower back (also known as the "waist").

In certain embodiments of the invention, the clamping device 20 set forth in FIGS. 3A and 3B can be used in the process where a suction device is not employed.

After collecting the fluid from the subcutaneous tissue layer, the SVF-containing fluid is transferred into a device that is identical to the device used to process BMA material or into a 60 cc syringe that has been designed to have a rounded profile at the base of the Luer-lok end of the syringe. Either device is placed in an appropriate holder that is subsequently inserted into a centrifugation system and the devices are spun. Any cells present in the devices will collect at a point within the device furthest from the axis of centrifugation. Once the centrifugation step has been completed, the spun devices are removed from the centrifugation system and placed in a yoke that is designed to support the devices (BMA-type device or syringe) in a secure manner. As a result of the centrifugation force, any cells present in the fluid will be pelleted at a point within the device furthest from the axis of centrifugation. The yoke is designed to hold each device securely, but is connected to a vibrating piece, such that when the vibration is activated, the pelleted cells will be gently resuspended. Collection of the pelleted cells is accomplished by use of a syringe that is attached to or has been attached to the outlet port of a collection device. The plunger of the syringe is pulled back just as the vibrating piece is activated, in such a manner that the resuspended cells are pulled into the receiving syringe with a minimum of fluid. Volume of fluid collected in the receiving syringe is variable and will depend on the treatment application.

Combination of the BMC and the SVF Cell Preparations

The collection of BMA and subcutaneous tissue layer fluid and the processing of these cell-containing suspensions to produce BMC and SVF will be accomplished off the sterile field.

Embodiments of the method are directed to the separate collection of bone marrow and adipose tissue, followed by their combination to form a composition that can be used in patient therapy.

In certain embodiments of the invention, the two cell preparations can be provided to the surgeon or the surgical team, who in turn will mix together the cell preparations with an autologous fluid like platelet poor plasma (PPP) or plasma protein concentrate (PPC) in proportions depending on the application.

In another embodiment of the claimed invention, the cell preparations can be passed onto the sterile field, if one has been established, along with the autologous PPP and/or PPC so that the surgeon or surgical staff can perform the combination of the two cell preparations with the PPP and/or PPC. Once combined, the preparation can be provided to the patient in order to augment the surgical or non-surgical treatment.

It also is contemplated that a means to assess the cell preparations for the number of cells present, their viability and the type of cells present in each preparation will be used. Some of the assays contemplated for assessing cell preparations of the type described herein include, but are not limited to, assessing the clusters of differentiation present with the cells by the use of appropriate reagents and sensing instrumentation (e.g., flow cytometry), placing an aliquot of the cell preparations into in vitro culture under conditions to assess their ability to differentiate into various cell lineages (e.g., adipo-, osteo-, chondro-), or to form colonies that can be counted or themselves differentiated in order to determine the frequencies of certain types of cells that are present. Other assays contemplated for use in analyzing the cell preparations include assays that demonstrate functional properties of the cell preparations like the induction of migration of test cells in vitro, rescue of apoptotic cells in vitro and secretion of various proteins and growth factors in vitro.

Working Examples

Example 1

Figure 5:
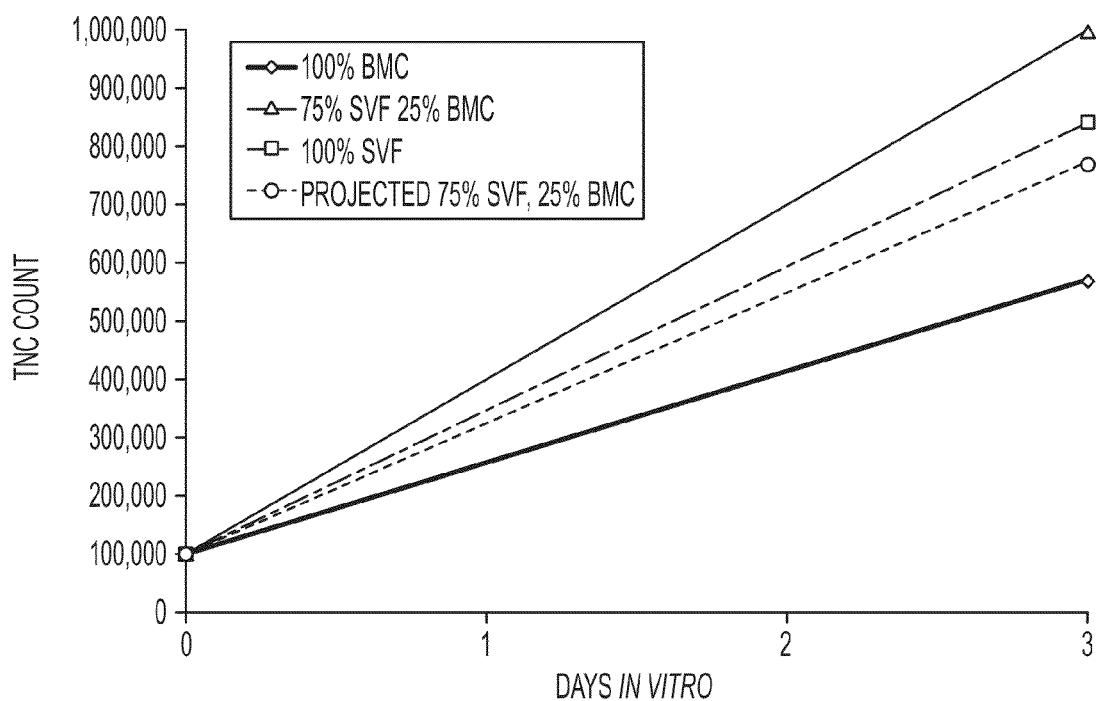
FIG. 5 represents a graph showing cell proliferation in vitro through 3 days for 100% bone marrow concentrate (BMC) and stromal vascular fraction (SVF) cells and combinations of 25% BMC/75% SVF.

Cells from different tissue sources are pre-conditioned based on their microenvironment of origin. For example, progenitor cells from the bone marrow (BMC) and stromal vascular fraction (SVF) of adipose tissue grow (proliferate) at specific rates. Based on the growth rate of each population, one can interpolate the number of cells from a mixed population based on the percentage inputs of each cell type. However, when mixed cell populations are cultured together, they often proliferate at a greater rate than the projected interpolation. FIG. 5 demonstrates the proliferation of BMC and SVF cells (100% populations) as TNC (total nucleated cell) counts and the projected and actual growth rates for various mixed populations. The projected proliferation rates for mixed populations are based on the weighted average of the pure populations. The Day 3 proliferation cell counts and the fold increase over projections for mixed populations are listed in Table 1.

Table 1 shows the in vitro proliferation of BMC and SVF cells at 3 days after initial seeding of 100,000 total cells per sample. Projected cell counts are based on a weighted average of 100% BMC and 100% SVF cell counts. The fold increase represents actual cell counts divided by projected cell counts.

TABLE 1

| Population | Day 3 Cell Counts | Projected Cell Counts | Fold Increase |
|---|---|---|---|
| 100% BMC | 569,000 | n/a | n/a |
| 75% SVF, 25% BMC | 998,000 | 773,750 | 1.29 |
| 100% SVF | 842,000 | n/a | n/a |

Example 2

Mesenchymal cells are defined by ability to form colonies (CFU-F) in vitro. Primary cells harvested from human bone marrow concentrate (BMC) or stromal vascular fraction (SVF) were cultured at densities to yield a detectable number of colonies after 10 days in vitro. BMC and SVF cells were grown independently and together at various concentrations. After 10 days, the average number of colonies was counted for each concentration of cells (Table 2, n=3 per dilution). Adding the average number of colonies from 250,000 BMC cells (3) and 5,000 SVF cells (16.3) yields a projected number of 19.3 colonies, but the actual count of the mixed population was 28, representing a 1.45 fold increase. A greater fold increase (2.23 fold) was demonstrated for mixed populations with a lower relative starting number of SVF cells.

Table 2 shows the average number of CFU-F colonies for each preparation of human BMC and SVF cells, the projected number of colonies based on weighted average of pure BMC and SVF cultures, and the fold increase due to the synergistic effect of mixed cell preparations.

TABLE 2

| Population | Average Number of Colonies | Projected Number of Colonies in Mixed Population | Fold Increase due to Synergistic Effect |
|---|---|---|---|
| 250,000 BMC cells | 3 | n/a | n/a |
| 5,000 SVF cells | 16.3 | n/a | n/a |
| 250,000 BMC cells + 5,000 SVF cells | 28 | 19.3 | 1.45 |
| 250,000 BMC cells + 1,000 SVF cells | 14 | 6.3 | 2.23 |

Mesenchymal cells are also defined by their ability to differentiate into bone and cartilage. In analogous assays to the CFU-F, primary colonies from human BMC and SVF were cultured osteogenic (bone-forming) or chondrogenic media for 10 days to produce CFU-O and CFU-C, respectively. CFU-O colonies were stained for alkaline phosphatase (ALP) activity and mineralization (alizarin red). CFU-C colonies were stained for glucosaminoglycan (GAG) extracellular matrix (alcian blue) and cellularity (nuclear fast red). The total number of colonies in each assay type was increased above the projected or interpolated value based on pure BMC and SVF colonies. In CFU-O colonies, synergy provided a substantially greater percentage of ALP activity than either cell type individually (Table 3). Similar trends were observed for mineralization in CFU-O and extracellular matrix in CFU-C.

Table 3 shows the average area stained positively for mineralization (alizarin red after CFU-O assay), ALP activity (CFU-O assay), and cartilaginous extracellular matrix proteins (alcian blue after CFU-C assay) for cell preparations of human BMC, SVF, and two mixed populations. Projected areas interpolated based on pure BMC and SVF data. Fold increase represents actual expression divided by projected value.

TABLE 3

| Cell Preparation | Average Area | Projected Area | Fold Increase |
|---|---|---|---|
| CFU-O Assay Mineralization | | | |
| 250k BMC | 23.2 | n/a | n/a |
| 1k SVF | 77.1 | n/a | n/a |
| 250k BMC + 1k SVF | 114.6 | 100.3 | 1.14 |
| 100k BMC + 1k SVF | 95.4 | 86.4 | 1.10 |
| CFU-O Assay ALP Activity | | | |
| 250k BMC | 28.3 | n/a | n/a |
| 1k SVF | 24.8 | n/a | n/a |
| 250k BMC + 1k SVF | 106.5 | 53.0 | 2.01 |
| 100k BMC + 1k SVF | 75.8 | 36.1 | 2.10 |
| CFU-C Assay Cartilage Extracellular Matrix | | | |
| 250k BMC | 6.8 | n/a | n/a |
| 1k SVF | 75.5 | n/a | n/a |
| 250k BMC + 1k SVF | 101.2 | 82.3 | 1.23 |
| 100k BMC + 1k SVF | 95.3 | 78.2 | 1.22 |

Example 3

The application of two cell preparations can be provided at the point-of-care for clinical applications such as in surgery. One such method comprises drawing 120 mL bone marrow aspirate and preparing a 10 mL aliquot of BMC. During the same surgical procedure, SVF cells can be harvested by a lipoaspirate technique and concentrated to a 5 mL cell solution. This combination of autologous BMC and SVF cells has been utilized to treat spinal cord injury by intrathecal injection, osteoarthritis by injection into the knee and shoulder, pain related to degenerative disc disease by intervertebral disc injection, and auto-immune disease by intravenous injection of the mixed cell preparation.

What is claimed is:
1. A method for treating a human subject with a combination cell therapy comprising bone marrow derived stromal cells and adipose tissue derived stromal cells, the method comprising:
   isolating stromal cells compatible with the subject, the isolating comprising:

aspirating bone marrow from the subject with a heparin-coated needle;

collecting adipose tissue from the subject, the collecting comprising a suction device comprising a first valve adapted to control a pressure within an inner space of the suction device and a second valve adapted to control a pressure in an annular-shaped peripheral suction chamber disposed about the rim of the suction device to aid in sealing the suction device to the subject, and further comprising a recovery cannula;

combining stromal cells isolated from bone marrow with stromal cells isolated from adipose tissue to form a therapeutic composition; and administering said therapeutic composition to the subject.

2. The method of claim 1, wherein the stromal cells are isolated from at least two different sources.

3. The method of claim 1, further comprising the steps of:
obtaining blood compatible with the subject; and
fractionating said blood to produce a blood component, said blood component selected from the group consisting of platelet-poor plasma, concentrated platelet-poor plasma, platelet-rich plasma, and combinations thereof.

4. The method of claim 3, wherein said blood component is combined with the isolated stromal cells to form a therapeutic composition.

5. The method for treating a human subject according to claim 1, wherein said stromal cells are isolated from tissue obtained from said subject.

6. The method for treating a human subject according to claim 1, wherein said stromal cells are washed at least once with a fluid selected from the group consisting of platelet-rich plasma, platelet-poor plasma, concentrated platelet-poor plasma, whole blood, and combinations thereof.

7. The method for treating a human subject according to claim 1, wherein the isolated stromal cells are able to differentiate into cells selected from the group consisting of chondrocytes, endothelial cells, osteoblasts, myocytes, neural cells, glial cells, adipocytes, pericytes, cardiomyocytes, epithelial cells, fibroblasts, and combinations thereof.

8. The method for treating a human subject according to claim 1, further comprising administering to the subject an additive selected from the group consisting of a cytokine, bioactive material, scaffold, buffer, or combinations thereof.

9. The method for treating a human subject according to claim 1, wherein the peripheral rim of the suction device is flat.

10. The method for treating a human subject according to claim 1, wherein the peripheral rim of the suction device is contoured to provide improved engagement with a portion of the subject that is not flat.

11. The method for treating a human subject according to claim 1, wherein the peripheral rim of the suction device further comprises an O-ring placed in a track that is adjacent to the annular-shaped peripheral suction chamber.

* * * * *